(12) United States Patent
Moukhina et al.

(10) Patent No.: US 10,168,291 B2
(45) Date of Patent: Jan. 1, 2019

(54) METHOD AND APPARATUS FOR THE THERMOMECHANICAL ANALYSIS OF A SAMPLE

(71) Applicant: Netzsch-Gerätebau GmbH, Selb (DE)

(72) Inventors: Elena Moukhina, Selb (DE); Doreen Rapp, Schönwald (DE); Markus Meyer, Ehingen (DE); Thilo Hilpert, Selb (DE); Martin Hager, Weissenstadt (DE); Fabian Wohlfahrt, Rehau (DE)

(73) Assignee: Netzsch-Gerätebau GmbH, Selb (DE)

( * ) Notice: Subject to any disclaimer, the term of this patent is extended or adjusted under 35 U.S.C. 154(b) by 124 days.

(21) Appl. No.: 15/201,737

(22) Filed: Jul. 5, 2016

(65) Prior Publication Data
US 2017/0003236 A1 Jan. 5, 2017

(30) Foreign Application Priority Data
Jul. 3, 2015 (DE) .................... 10 2015 008 654

(51) Int. Cl.
*G01N 25/16* (2006.01)
(52) U.S. Cl.
CPC .................... *G01N 25/16* (2013.01)
(58) Field of Classification Search
CPC ..................................... G01N 25/16
See application file for complete search history.

(56) References Cited

U.S. PATENT DOCUMENTS 6,007,240 A 12/1999 Price
2002/0136262 A1* 9/2002 Feger ............... G01N 25/16
374/55

* cited by examiner

*Primary Examiner* — Manuel A Rivera Vargas
(74) *Attorney, Agent, or Firm* — Whitmyer IP Group LLC

(57) ABSTRACT

A method for the thermomechanical analysis of a sample (P) of a material including (a) controlling the temperature of the sample (P), (b) recording data representative for a length variation (dL) of the sample (P), (c) evaluating the data in order to determine a reversible component ($dL_{rev}$), (d) calculating a corrected reversible component ($dL_{rev\text{-}corr}$; $\alpha_{rev\text{-}corr}$) and/or of the coefficient of thermal expansion ($\alpha$).

12 Claims, 8 Drawing Sheets

METHOD AND APPARATUS FOR THE THERMOMECHANICAL ANALYSIS OF A SAMPLE

TECHNICAL FIELD

The present invention relates to a method for the thermomechanical analysis of a sample as well as an apparatus for thermomechanical analysis.

BACKGROUND

In a thermomechanical analysis, frequently also designated as TMA ("thermomechanical analysis"), one or more mechanical properties of a sample of a material are measured as a function of the temperature.

The material can be, for example, a solid, liquid or pasty material. Frequently here, for example, a length variation is measured as a function of the temperature and/or time under well-defined mechanical loading of the sample, wherein the sample is usually exposed to a predetermined time-dependent temperature, i.e. a "temperature programme".

In particular, in the case of an almost negligible (relatively small) mechanical loading of the sample, e.g. only caused by using a sensing stamp or the like to measure the length variation, the TMA is frequently also designated as dilatometry or when using a modulated temperature program as temperature-modulated dilatometry.

In a TMA of the type of interest here, a "modulated temperature programme" is used, which means that the time profile of the temperature is composed of a basic, usually linearly predefined temperature variation corresponding to a "basic heating rate" and of a usually sinusoidal (alternatively feasible e.g. triangular, rectangular or sawtooth-shaped) predefined temperature modulation superimposed on this temperature variation.

An important aim of a TMA of the type of interest here is to determine for the material of the sample at least one "reversible component" of the length variation (caused by temperature variation) and/or in particular e.g. a reversible component of the coefficient of thermal expansion.

Since, if the sample is exposed to a thermally induced conversion process (e.g. phase transition, glass transition, sintering process etc.) during the thermomechanical analysis, a directly measured "total component" of the length variation or of the coefficient of thermal expansion is additively composed of a "reversible component" and a "non-reversible component", after determining the "reversible component", the "non-reversible component" of the length variation or of the coefficient of thermal expansion can be determined simply (by subtracting the reversible component from the total component).

The temperature-dependent determination and characterization of shrinkage or expansion effects of the sample or the influence of such effects on the length variation or the coefficients of thermal expansion is in practice frequently a "main aim" of the TMA.

A generic method for thermomechanical analysis is described, for example, in U.S. Pat. No. 6,007,240 and comprises the following steps:
a) arranging the sample in a thermomechanical analysis device and controlling the temperature of the sample by means of the analysis device according to a modulated temperature program,
b) recording data obtained by means of the analysis device which is representative for a length variation of the sample in the course of the temperature control,
c) evaluating the data in order to determine a reversible component of the length variation and/or a reversible component of the coefficient of thermal expansion of the sample,
d) calculating a corrected reversible component of the length variation by means of a correction parameter which is calculated as the ratio of a total length variation and a reversible component of the length variation.

FIGS. 1 to 3 show as an example a combination of a linear temperature variation (FIG. 1) and a sinusoidal temperature modulation (FIG. 2) for implementing a modulated temperature program (FIG. 3). In FIGS. 1 to 3 the time t is plotted on the right and the temperature T at the top.

FIGS. 1 to 3 show a linear variation of the temperature T which can be described as follows: $T=T_0+(\beta \times t)$. Here $T_0$ denotes an initial temperature and $\beta$ the heating rate. In the example of FIG. 1 the heating rate $\beta$ is 2.0 K/min. It should be noted that here and also in the following description of the invention, for simplicity there is always talk of a heating rate $\beta$ although this heating rate $\beta$ can also be specified as negative (i.e. corresponding to a "cooling rate").

FIG. 2 shows a sinusoidal variation of the temperature T which can be described as follows: $T=T_{avg}+A_T \times \sin(\omega t)$. Here $T_{avg}$ denotes an averaged (over the period duration) temperature. $A_T$ denotes an amplitude of the temperature modulation, $\omega$ denotes a modulation frequency. In the example of FIG. 2, $T_{avg}$ is about $-1.2°$ C., $A_T$ is 1.5 K and $\omega$ is about 2.1 min$^{-1}$ (corresponding to a period duration of 3.0 min).

FIG. 3 shows the modulated temperature program corresponding to a superposition of the linear variation (FIG. 1) and the sinusoidal variation (FIG. 2), which can be described as follows: $T=T_0+(\beta \times t)+A_T \times \sin(\omega t)$.

In a TMA thus carried out, all the parameters of the modulated temperature program (here therefore: $T_0$, $\beta$, $A_T$ and $\omega$) are defined (preset) by a user adapted, for example, to the specific application.

Even in a modulated temperature program, an averaged (over the period duration) temperature $T_{avg}$ can be specified. For this it holds that: $T_{avg}=T_0+(\beta \times t)$. Thus, the modulated temperature program can be described as follows: $T=T_{avg}+A_T \times \sin(\omega t)$.

If a temperature deviation $\Delta T=A_T \times \sin(\omega t)$ is defined to describe the modulation-induced "temperature oscillations", the modulated temperature program can described as follows: $T=T_{avg}+\Delta T$.

The "coefficient of thermal expansion $\alpha$" is an important characteristic value which describes the behaviour of a material in relation to variations of its dimensions with temperature variations. The coefficient of thermal expansion $\alpha$ (only dependent on temperature) is a substance-specific material constant which is usually more or less strongly temperature-dependent. The coefficient of thermal expansion $\alpha$ is understood here in the sense of a coefficient of length expansion (unlike the frequently used volumetric thermal expansion coefficient $\gamma$) and is the proportionality constant between the temperature variation dT and (reversible) relative length variation dL/L of the material: $dL/L=\alpha \times dT$. Accordingly it holds that:

$$\alpha = \frac{1}{L} \times \frac{dL}{dT}.$$

In the situation according to FIG. 1 (linear temperature variation) it holds that $dL=L\times\alpha\times dT$ and $dT=\beta\times dt$ and therefore: $dL=L\times\alpha\times\beta\times dt$.

From this the coefficient of thermal expansion α can be determined as follows:

$$\alpha = \frac{1}{L\beta} \times \frac{dL}{dT}$$

The linear profile of the length variation $dL/L_0$ in FIG. 1 as a function of the time t is equivalent to the fact that a in this (idealized) example is a temperature-independent constant.

In the situation according to FIG. 3 (modulated temperature program with linear basic heating), for the length variation there are two components, namely an "underlying component" (caused by the basic heating rate $\beta\neq 0$) and an "oscillating component" (caused by the temperature oscillations). An "underlying dL" can be calculated as an average over the period and is designated hereinafter as $dL_{total}$. Here it holds that $dL_{total}=L_{total}\times\alpha\times dT_{avg}$ and $dT_{avg}=\beta\times dt$ and therefore: $dL_{total}=L_{total}\times\alpha\times\beta\times dt$.

From this the coefficient of thermal expansion atom, can be determined from $dL_{total}$ as follows:

$$\alpha_{total} = \frac{1}{L_{total}\beta} \times \frac{dL_{total}}{dt} \quad \text{(Formula 1)}$$

The linear behaviour of the length variation $L_{total}/L_0$ as a function of the time t in FIG. 3 is equivalent to the fact that $\alpha_{total}$ in this (idealized) example is a temperature-independent constant.

In the situation according to FIG. 2 (temperature modulation) assuming that "T" is the uniform temperature of the relevant material sample, it also holds that $\Delta L=L\times\alpha\times\Delta T$, and $\Delta T=A_T\times\sin(\omega t)$, from which it follows for the "length variation" $\Delta L$:

$\Delta L=L\times\alpha\times A_T\times\sin(\omega t)$.

However, this is only correct for an "ideal" situation in which the sample temperature in each point of the same is the same, i.e. in particular for example in the centre and on the surface of the sample. However, this is not the case in practice since it would assume that the modulation frequency ω is infinitely small or the thermal conductivity of the sample material was infinitely high.

If an amplitude of the length variation is defined as $A_L$ to describe the modulation-induced "length oscillations", it thus holds that:

$\Delta L = A_L \times \sin(\omega t)$.

$A_L$ is the amplitude of the measured modulated length variations. It can be calculated from a representative measurement signal for these length variations, e.g. by a Fourier analysis (e.g. "Fast Fourier Transformation").

From this the (reversible) coefficient of thermal expansion $\alpha_{rev}$ can be determined as follows from the oscillating component of the measurement signal theoretically for an ideal situation as follows:

$$\alpha_{rev} = \frac{1}{L} \times \frac{A_L}{A_T} \quad \text{(Formula 2)}$$

In practice however, the problem manifest in the example of FIG. 2 arises that the temperatures in different areas of the sample differ more or less from one another and from the temperature behaviour which is predefined by a temperature-control device used in the thermomechanical analysis device used according to the modulated temperature program. As a result of the heating and cooling of the sample taking place from outside, in practice a more or less large temperature gradient which cannot be neglected always forms inside the sample.

Thus, in practice, as a result of the not infinitely rapid heat conduction of heat into the sample and out from the sample, this results, for example, in a "lagging" of the same temperature which in FIG. 2 leads to a time shift of the length oscillations (curve dL) relative to the temperature oscillations (curve T). At the same time, this effect has the result that the average value (averaged over entire sample) of the temperature amplitude $A_T$ is lower than that predefined by the temperature program. This in turn has the result that the amplitude of the length variation $A_L$ is smaller.

In reality the temperature amplitude at the centre of the sample is smaller than the predefined (e.g. by a user by corresponding setting) temperature amplitude $A_T$ on the sample surface. Therefore the amplitude of the length oscillations of the sample AL is smaller than in the mentioned ideal situation and the length oscillations are delayed relative to the temperature oscillations. For real modulations a frequency-dependent complex calibration coefficient (correction coefficient) k is required to obtain the corrected reversible coefficient of thermal expansion $\alpha_{rev-corr}$:

$\alpha_{rev-corr}=k\times\alpha_{rev}\Delta L=k\times L_{total}\times\alpha_{rev}\times A_T\times\sin(\omega t)$. (Formula 3)

If a modulated temperature program (e.g. of the type shown in FIG. 3) is used which additionally includes the basic, e.g. linear temperature variation (cf. FIG. 1), such a "calibration" can advantageously be performed so that a calibrated determination of the coefficient of thermal expansion α is possible:

$$\alpha_{rev-corr} = \frac{1}{L_{total}} \times \frac{1}{k} \times \frac{A_L}{A_T} \quad \text{(Formula 4)}$$

In general and in particular if the sample is subjected to a thermally induced conversion process at the temperature or temperature variation in the course of the thermomechanical analysis, a (directly measured) "total" length variation $dL_{total}$ has a "reversible" component $dL_{rev}$ and a "non-reversible" component $dL_{nonrev}$, and it holds that: $dL_{total}=dL_{rev}+dL_{nonrev}$.

$dL_{total}$ can be calculated as an average (e.g. averaged over precisely one period) of the time-resolved measured value of dL.

$dL_{rev}$ can be calculated as $dL_{rev}=dL_{o\ rev}+L_o\times\int_{T_o}^{T}\alpha_{rev}dT$, where $dL_{o\ rev}$ is the reversible length variation at the beginning of the temperature segment. At the beginning of the measurement, it holds that: $dL_{rev}=0$.

Accordingly a "total" coefficient of thermal expansion $\alpha_{total}$ which can be obtained directly from an analysis of $dL_{total}$, has a "reversible" component $\alpha_{rev}$ and a "non-reversible" component $\alpha_{nonrev}$, and it holds that: $\alpha_{total}=\alpha_{rev}+\alpha_{nonrev}$.

In FIGS. 1 to 3 assuming a purely reversible thermal expansion ($dL_{total}=dL_{rev}$, $dL_{nonrev}=0$, $\alpha_{total}=\alpha_{rev}$, $\alpha_{nonrev}=0$), it is therefore equivalent that the sample is not subjected to any thermally induced conversion process in the thermomechanical analysis (e.g. a sample made of metal), in each case the resulting relative length variations $dL/L_0$ are additionally plotted at the top, where $L_0$ denotes an initial length of the sample being analysed (the difference between L and $L_0$ is in practice mostly negligible).

Assuming that in the thermomechanical analysis the sample is not subject to any thermally induced conversion process ($\alpha_{total}=\alpha_{rev-corr}$), the correction parameter k can be calculated from formulas (1) and (3) as the quotient of the "total expansion coefficient" $\alpha_{total}$, which characterizes a "total averaged length variation $\Delta L_{avg}$" (considered over a relatively large temperature variation $\Delta T_{avg}$) and the "reversible expansion coefficient" $\alpha_{rev}$, which characterizes a "reversible component $dL_{rev}$ of the length variation" dL (considered over a relatively small temperature variation dT):

$$k=\alpha_{total}/\alpha_{rev} \quad \text{(Formula 5)}$$

The quantities $\alpha_{total}$ and $\alpha_{rev}$ required to determine the correction parameter k can be obtained as follows:

$$\alpha_{total}=1/L_{total} \times dL_{total}/T_{avg} \text{ and } \alpha_{rev}=1/L_{total} \times A_L/A_T$$

By means of the correction parameter k determined in this way, a corrected reversible component $dL_{rev-corr}$ of the length variation dL or a corrected reversible component $\alpha_{rev-corr}$ of the (reversible) coefficient of thermal expansion $\alpha_{rev}$ can be calculated (cf. above formula 4).

This method fails however if the sample is subjected to a thermally induced conversion process in the course of the modulated temperature program.

SUMMARY

It is the object of the present invention, in a TMA of the type mentioned initially and described, for example, in U.S. Pat. No. 6,007,240 to enable the calculation of a corrected reversible component of the length variation and/or a corrected reversible component of the coefficient of thermal expansion also for regions in which the sample is subjected to a thermally induced conversion process in the thermomechanical analysis.

This object is solved in the method according to the invention whereby the temperature program has a first segment with a first basic heating rate and the correction parameter is calculated using data from the first segment in a temperature-dependent manner from an estimate of a temperature-dependent function of the said ratio in a region of the first segment in which the sample is not subjected to any thermally induced conversion process, and that the temperature program has a second segment with a second basic heating rate lower, for example, compared with the first basic heating rate and the correction parameter calculated using the data from the first segment is used to calculate the corrected reversible component of the length variation and/or the coefficient of thermal expansion in the second segment.

The invention is therefore based on the idea of calculating the correction parameter including its "temperature dependence" in a suitable (first) segment of the temperature program for this purpose and then using this calculation result for determining or calculating the correction parameter used in the other (second) segment of the temperature program. This is possible even if the sample is (at least) subjected to a thermally induced conversion process in the second segment.

The use of the correction parameter calculated in a temperature-dependent manner in the first segment can be provided, e.g. by a type of extrapolation.

In one embodiment it is provided that the magnitude of the second basic heating rate is equal to the magnitude of the first basic heating rate. This can be disadvantageous in that—due to the temperature variation in the course of the second segment—using there the result of the correction parameter calculation originating from the first segment can bring with it a certain error.

In another embodiment in this respect it is therefore provided that the magnitude of the second basic heating rate, when considered in absolute terms, is relatively small and/or smaller than the magnitude of the first basic heating rate. In extreme cases even a second heating rate of zero can be provided.

Thus, against the background that the correction parameter is generally temperature-dependent, the afore-mentioned falsification can be avoided.

In one embodiment it is provided that the first basic heating rate is greater than zero (corresponding to a modulated heating of the sample in the first segment).

In one embodiment it is provided that the second basic heating rate is greater than or equal to zero (corresponding to a modulated heating or modulated keeping the sample temperature constant in the second segment).

In one embodiment it is provided that the magnitude of the first basic heating rate is greater than 0.5 K/min, in particular greater than 1 K/min, where this amount can however, for example, be less than 100 K/min, in particular less than 50 K/min.

In one embodiment it is provided that the magnitude of the second basic heating rate is less than 0.5 K/min, in particular less than 0.2 K/min.

In one embodiment it is provided that the magnitudes of the first basic heating rate and the second basic heating rate differ from one another by at least a factor of 2, in particular by at least a factor of 5.

In one embodiment it is provided that the sample is subjected to a thermally induced conversion process within the second segment.

In one embodiment it is provided that the temperature of the sample increases in the course of the second segment and exceeds a value of 500° C., in particular exceeds a value of 1000° C. This is advantageous insofar as in many materials, thermally induced conversion processes can only be expected at these relatively high temperatures which, however, can be advantageously investigated by means of the invention through an appropriate choice of the "second segment".

In one embodiment it is provided that when evaluating the data, a non-reversible component of the length variation is further determined. Alternatively or additionally, a nonreversible component of the coefficient of thermal expansion can be determined.

In one embodiment it is provided that for the correction parameter calculated using data from the first segment, a mathematical estimating function is modelled which gives the correction parameter as a function of the temperature of the sample and that by using the mathematical estimating function, the correction parameter to be used to calculate the corrected reversible component of the length variation, alternatively or additionally the corrected reversible component of the coefficient of thermal expansion is calculated in the second segment. The correction parameter used in the second segment is in this case therefore a parameter extrapolated from the first into the second segment by means of the estimating function.

In one embodiment it is provided that when calculating the estimating function a plurality of "support points" (preferably at least 2, in particular at least 5) are used in order to thus calculate a temperature-dependent estimating function for the correction parameter with relatively high accuracy.

For example, a linear function or, for example, a polynomial (e.g. parabola) is considered as estimating function.

In one embodiment the mathematical form of the estimating function used to evaluate the data is fixedly predefined. Alternatively a mathematical form which can be predefined or selected by the user can be used. In these cases, the "modelling" of the mathematical estimating function can be considered as a calculation of the relevant function parameters (e.g. by the "least squares" method or another adaptation algorithm).

On transition from a, for example, dynamic ($\Theta \neq 0$) first segment to a directly adjacent second, for example, isothermal ($\beta = 0$) segment or conversely, advantageously no discontinuity point appears in the temperature-dependent behaviour of the calculated correction parameter (and consequently also not in the behaviour of the calculated reversible quantities $dL_{rev}$ or $\alpha_{rev}$).

In one embodiment it is provided that in course of the temperature program, when considered in time, the second segment lies directly after the first segment or conversely.

In a preferred embodiment, a Fourier analysis is applied in order to determine averages, amplitudes and phase shifts (in relation to a first temperature signal) from the measured data relating to a signal representative of the length variation of the sample. A Fourier analysis, for example, has the advantage that influences of signal noise are not taken into account.

In order to determine averages, amplitudes and phase shifts, alternatively however consideration can, for example, also be given to accomplishing this on the basis of a determination of average and amplitudes without Fourier analysis. In this case, averages can be calculated, for example, as a mathematical average between directly adjacent maxima and minima.

A preferred application of the method according to the invention is so-called dilatometry, a special type of TMA in which the length variation of a sample under negligible application of force (e.g. a maximum force of 0.5 N) is determined in the narrower sense in a temperature-dependent manner. In addition, for example, an application within the framework of a DMA (dynamic mechanical analysis) also comes into consideration. DMA primarily aims to measure a deformation force on a sample as a function of the temperature and/or time under defined dynamic-mechanical deformation.

According to a further aspect of the invention, an apparatus for thermomechanical analysis of a sample of a material is provided comprising
  a sample holder for receiving the sample,
  a temperature-control device for controlling the temperature of the sample according to a modulated temperature program,
  a temperature-measuring device for measuring a temperature of the sample in the course of the temperature control,
  a length measuring device for measuring a length variation of the sample in the course of the temperature control,
  a data recording device for recording data which are representative for the length variation of the sample in the course of the temperature control and data which are representative for the variation in the temperature of the sample in the course of the temperature control,
  an evaluation device which is configured to determine a reversible component of the length variation and/or a reversible component of the coefficient of thermal expansion of the sample and/or to calculate a corrected reversible component of the length variation and/or of the coefficient of thermal expansion by means of a correction parameter which is calculated using a ratio determined from the data of a parameter characterizing a total length variation and a parameter characterizing the reversible component of the length variation,
characterized in that the temperature control device is configured, in the course of the temperature program, to provide a first segment with a first basic heating rate and a second segment with a second basic heating rate (e.g. lower compared with the first basic heating rate) and that the evaluation device is configured to calculate the correction parameter using data from the first segment in a temperature-dependent manner from an estimate of a temperature-dependent function of the said ratio in a region of the first segment in which the sample is not subjected to any thermally induced conversion process and to use the correction parameter calculated using the data from the first segment for calculating the corrected reversible component of the length variation and/or the coefficient of thermal expansion in the second segment.

The particular embodiments and further developments described for the method of analysis according to the invention can be provided individually and in any combination, in similar manner also as particular configurations or further developments of the analysis device according to the invention.

According to a further aspect of the invention, a computer program product is provided comprising a program code which is executed on a data processing device and performs a method of analysis of the type described here. Such a computer program product can be used in particular for programming or for sequence control of a control unit contained in the analysis device provided according to the invention.

BRIEF DESCRIPTION OF THE DRAWINGS

The invention is further described hereinafter by means of exemplary embodiments with reference to the appended drawings. In the figures.

DETAILED DESCRIPTION

Figure 1:
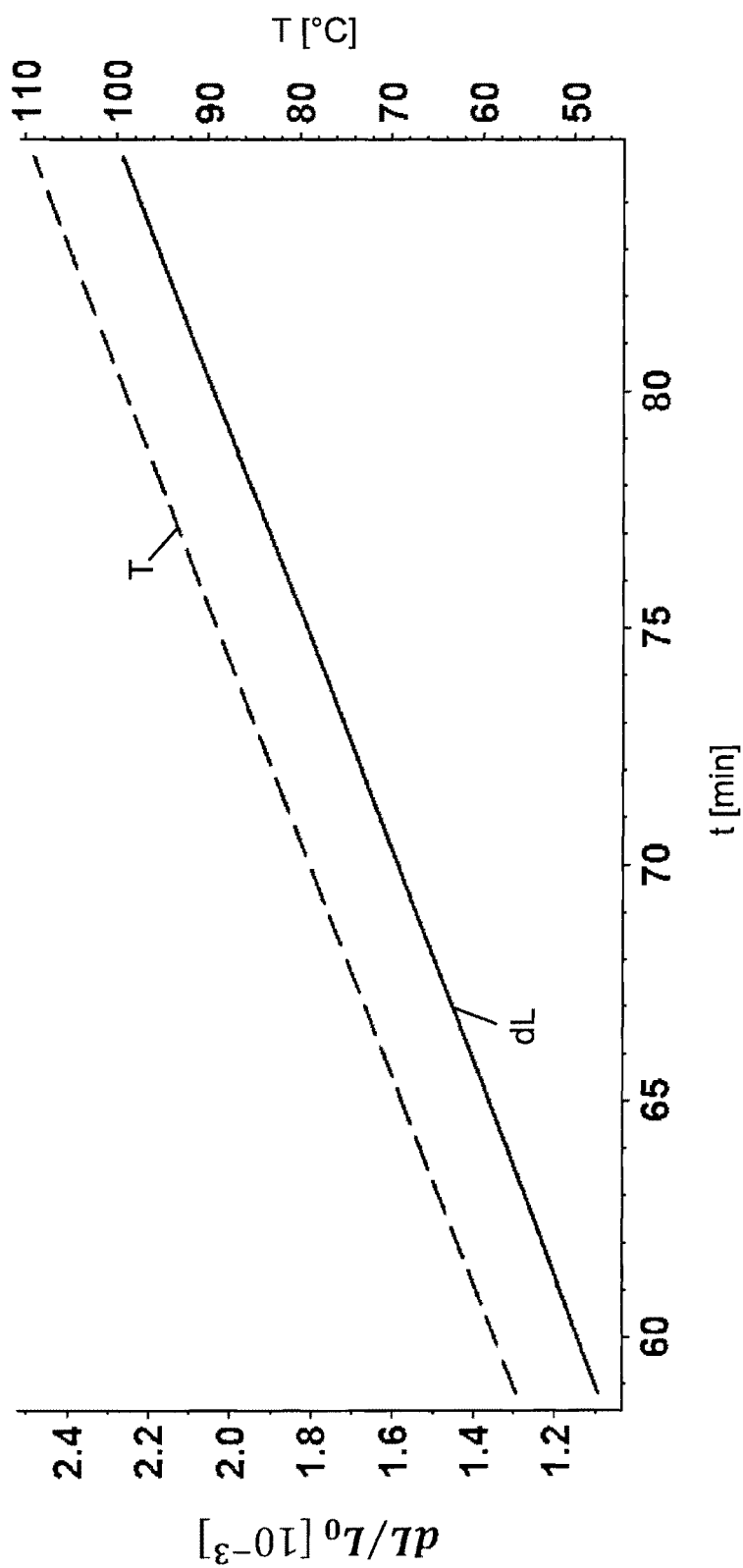
FIG. 1 shows a diagram to illustrate a linear temperature variation and the measurement of a length variation caused thereby on a sample.
Figure 2:
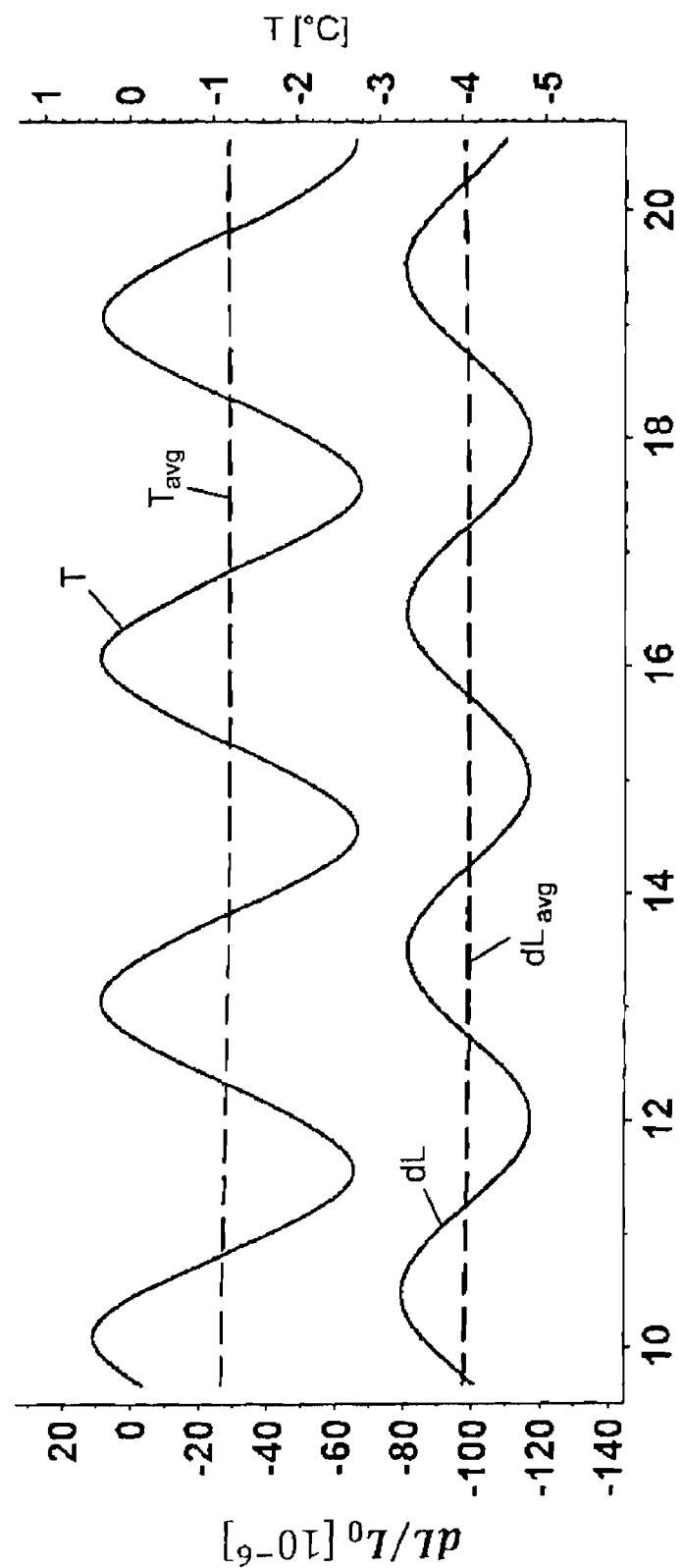
FIG. 2 shows a diagram to illustrate a sinusoidal temperature variation and the measurement of a length variation caused thereby on the sample.
Figure 3:
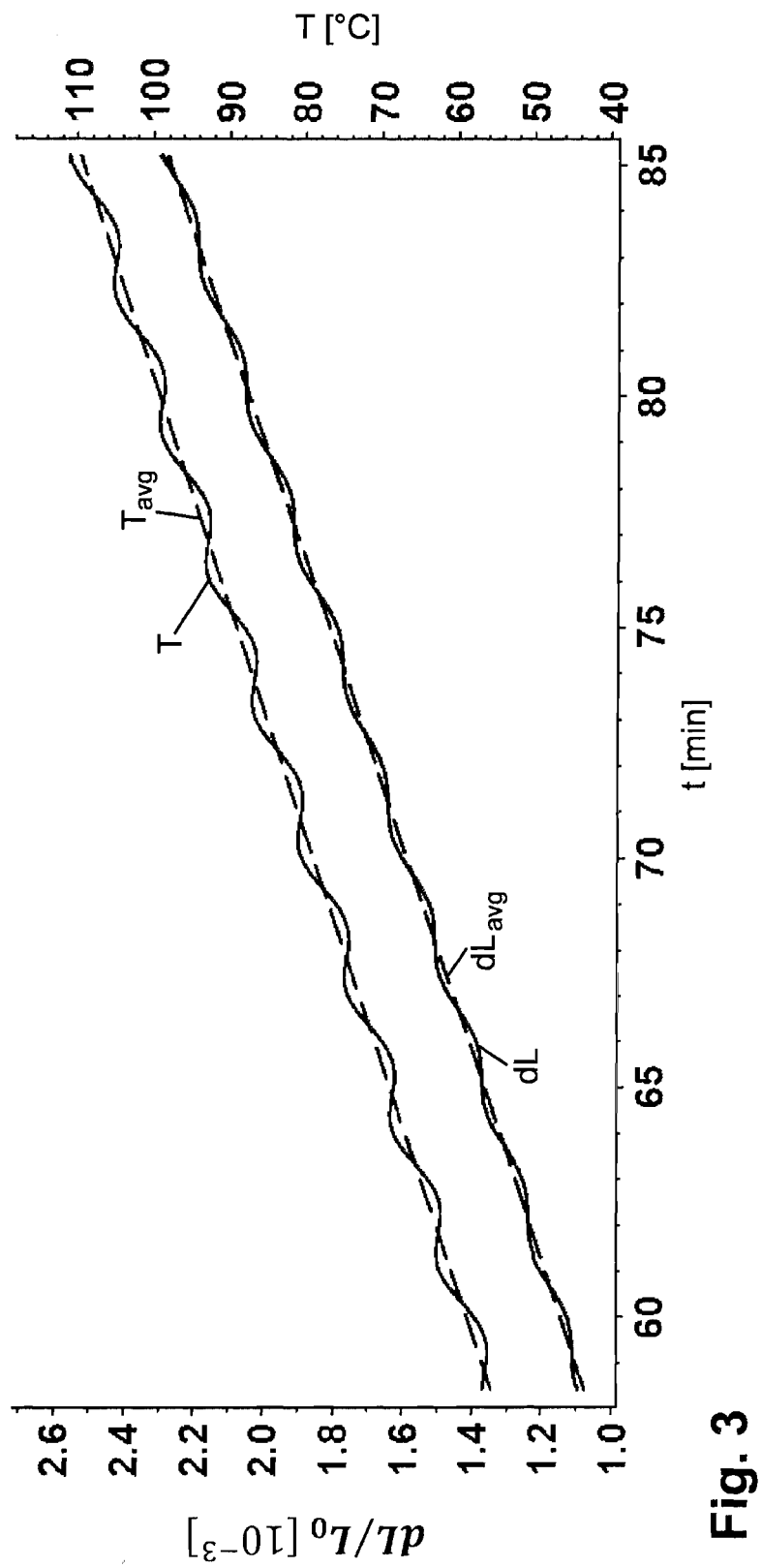
FIG. 3 shows a diagram to illustrate a modulated temperature program composed of a linear temperature variation (FIG. 1) and a temperature modulation (FIG. 2), and the measurement of a length variation caused thereby on the sample.

FIGS. 1 to 3 have already been explained further above and illustrate a linear temperature variation (FIG. 1), a temperature modulation (FIG. 2) and a modulated temperature program resulting from combining these temperature variations (FIG. 3).

Figure 4:
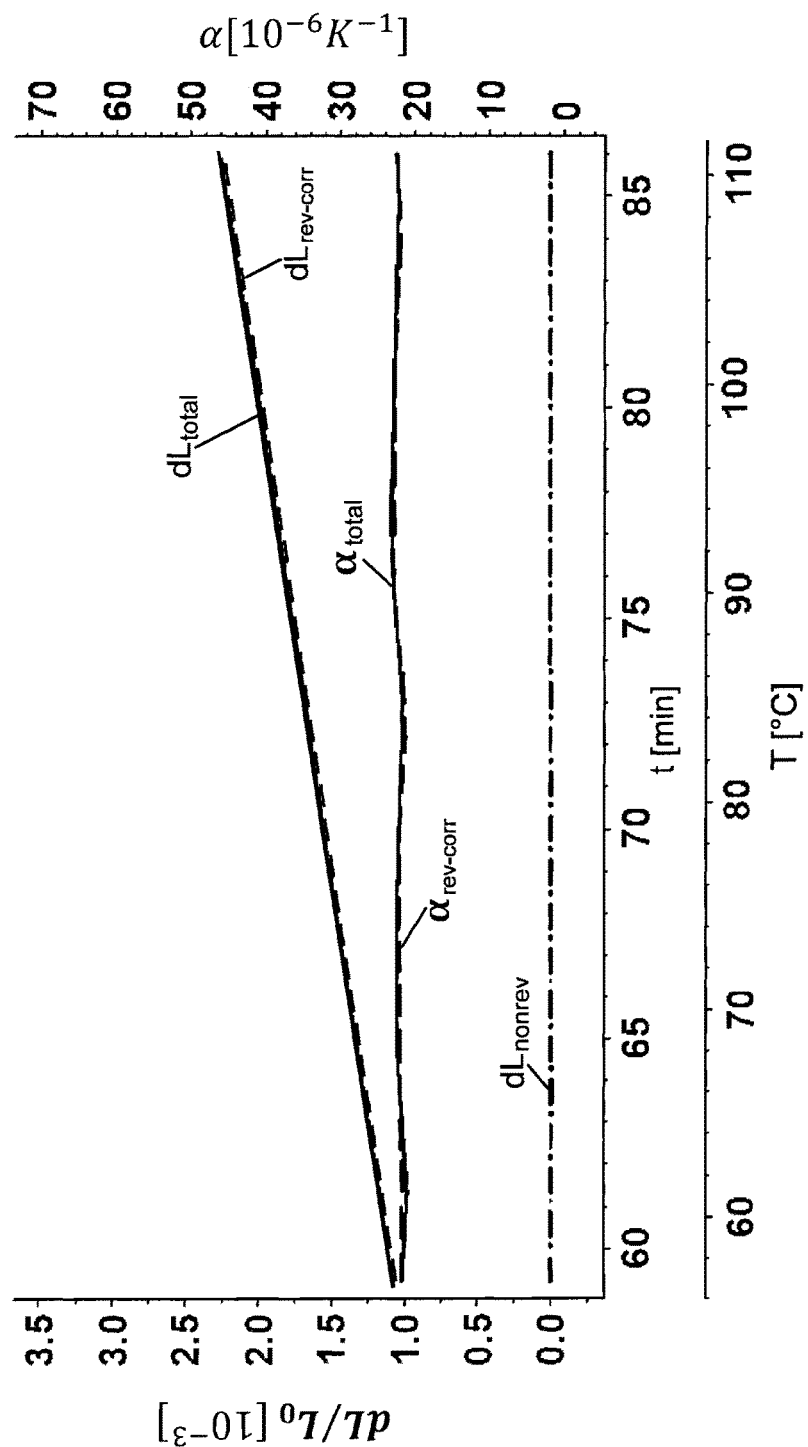
FIG. 4 shows a diagram to illustrate the result of a thermomechanical analysis according to a first example (sample made of metal)

FIG. 4 illustrates the result of thermomechanical analysis not according to the invention, according to the first example, in which the temperature program shown in FIG. 3 was used and the analytical sample consists of a metal which is not subject to any thermally induced conversion process over a temperature range of about 60-110° C.

In this respect, this example corresponds to the example already described according to FIG. 3 but in FIG. 4 in particular the time-dependent profiles of the corrected quantities $dL_{rev\text{-}corr}$ and $\alpha_{rev\text{-}corr}$ obtained by means of the mentioned correction parameter k are plotted as a result of the TMA.

Also plotted in FIG. 4 are the profiles of the total relative length variation $dL_{total}$ and the non-reversible relative length variation $dL_{nonrev}$. Here $dL_{nonrev}$ was obtained as $dL_{nonrev} = dL_{total} - dL_{rev\text{-}corr}$.

Finally the profile of the total coefficient of thermal expansion $\alpha_{total}$ is also plotted in FIG. 4.

Since the time-dependent behaviour of the temperature T, i.e. the "temperature program" is known, the profiles obtained according to FIG. 4 can readily be converted into temperature-dependent profiles of the plotted quantities. In the case of the basic heating rate β predefined as constant here, the profiles identifiable in FIG. 4 even correspond qualitatively exactly to the respective "temperature-dependent profiles" (cf. on this matter the temperature axis plotted additionally in FIG. 4). Otherwise, in the case of a non-constant basic heating rate, the time-dependent profiles could easily be "converted" taking into account the time-dependent profile of the averaged temperature $T_{avg}$.

The determination of the correction parameter k presents absolutely no problems in this example since the sample is not exposed to any thermally induced conversion process in the course of the modulated temperature program.

However, the invention aims to make it possible to calculate a corrected reversible component of the length variation $dL_{rev\text{-}corr}$ and/or a corrected reversible component of the coefficient of thermal expansion $\alpha_{rev\text{-}corr}$ even when the sample is exposed to a thermally induced conversion process. An example for this is shown in FIG. 5.

Figure 5:
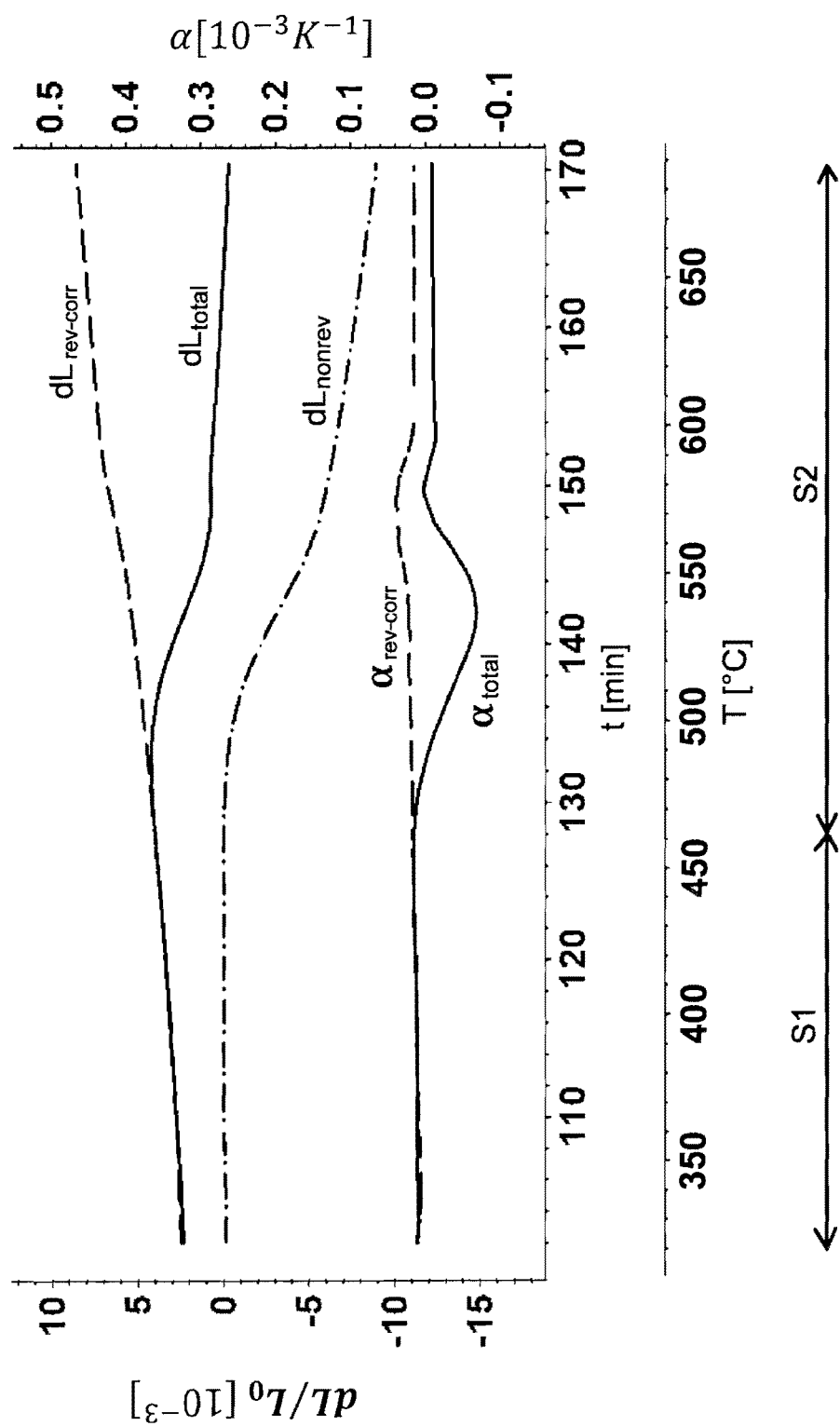
FIG. 5 shows a diagram to illustrate the result of a thermomechanical analysis according to a second example (sample made of ceramic)

FIG. 5 shows the result of a TMA according to the invention (here: dilatometry) according to an example in which a modulated temperature program was used and the analysed sample consists of a ceramic in which a thermally induced conversion process is to be expected at a temperature in the range of about 500-600° C. FIG. 5 shows a section of the TMA result for the temperature range of about 350° C. to 700° C.

A particular feature of this example is that the temperature program has a first segment S1 with a first basic heating rate β1 (here for example about 5 K/min) and the correction parameter k is calculated using data from this first segment S1 and that the temperature program has a second segment S2 with a second basic heating rate β2 (here for example about 5 K/min) and the correction parameter k calculated using data from the first segment S1 in a temperature-dependent manner is used to calculate the corrected reversible component $dL_{rev\text{-}corr}$ of the length variation dL in the second segment S2.

The correction parameter k calculated in the segment S1 of the temperature program suitable for this (in view of the lack of a thermally induced conversion process) is extrapolated to a certain extent into the adjoining second segment S2 towards higher temperature (and used there to calculate the profiles of $dL_{rev\text{-}corr}$ and $\alpha_{rev\text{-}corr}$).

For example, the value of k obtained as a result of the correction parameter calculation performed in the first segment S1 for the end of the first segment S1 (i.e at approximately t=128 min or T=460° C.) can be provided as the correction parameter k to be used over the entire second segment S2 for the correction. Preferably however, a mathematical function describing the temperature-dependent profile of the correction parameter k obtained in the first segment S1 is modelled as a result of the correction parameter calculation performed in the first segment S1 in order to then obtain the temperature-dependent correction parameter by inserting the temperatures prevailing in the second segment into this function for correction in the second segment S2 (extrapolation).

This advantageously allows the correction of the reversible quantities even in the second segment S2 although the sample there undergoes a thermally induced conversion process.

Unlike the example shown in which the basic heating rates β1, β2 of the segments S1, S2 are selected to be the same (β1=β2=5 K/min), any error in the correction extended to the segment S2 by "extrapolation" can be further reduced or avoided as a result of a temperature dependence of the correction parameter k by selecting the basic heating rate β2 used in the second segment S2 to be comparatively low (or even β2=0).

In the example shown in FIG. 5 by means of the recorded data from the first segment S1, the correction parameter k was calculated in the form of a temperature-dependent correction estimating function, for example by means of an adaptation known per se ("fit", e.g. using the least squares method or the like) of a predetermined mathematical function which gives the correction parameter k as a function of the temperature T of the sample. By means of this estimating function, the correction parameter k for use in the second segment S2 was then calculated and used there in order to obtain the profiles of $dL_{rev\text{-}corr}$ and $\alpha_{rev\text{-}corr}$ (and then from this the quantities plotted in FIG. 5).

Figure 6:
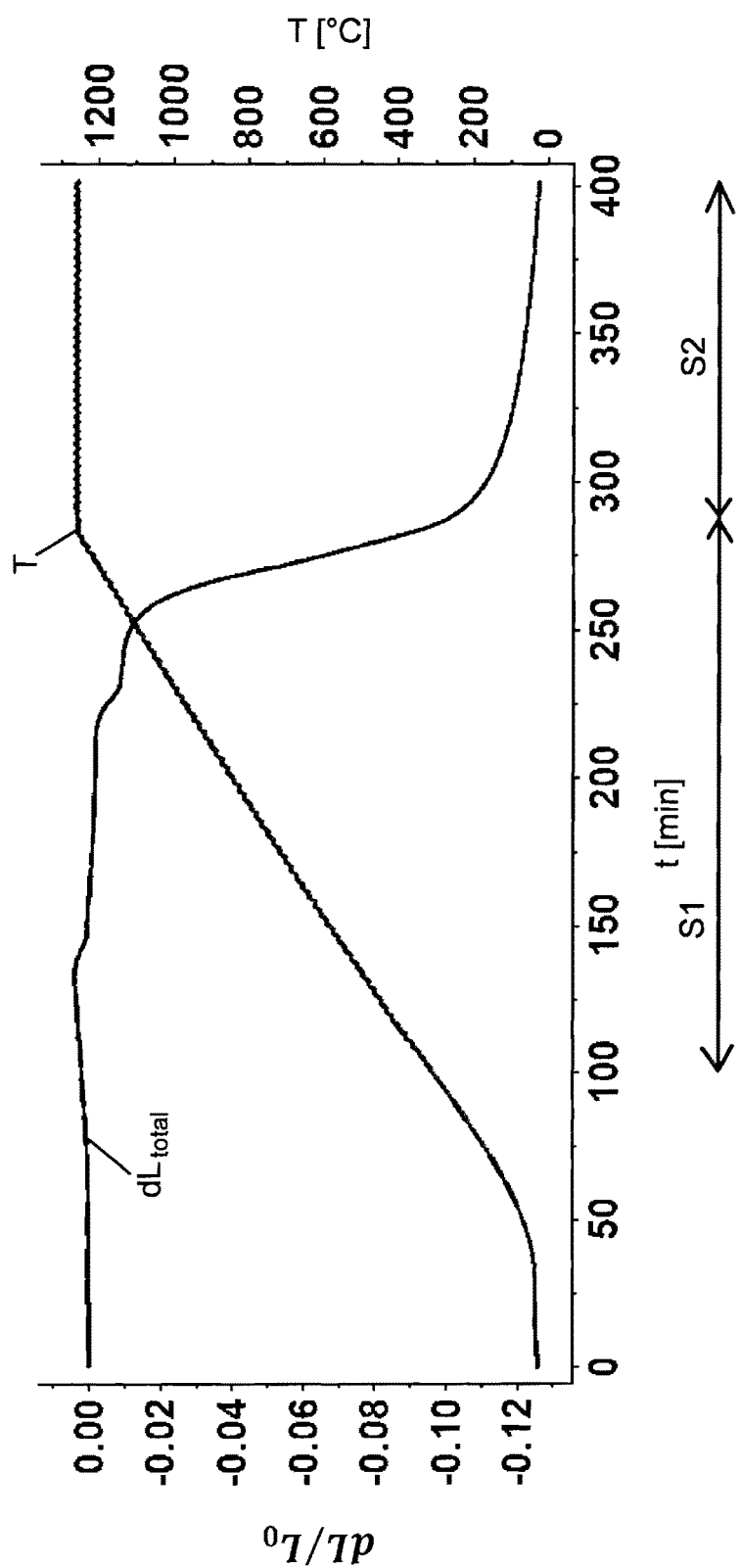
FIG. 6 shows a diagram to illustrate an intermediate result of a thermomechanical analysis according to a third example (sample made of ceramic)
Figure 7:
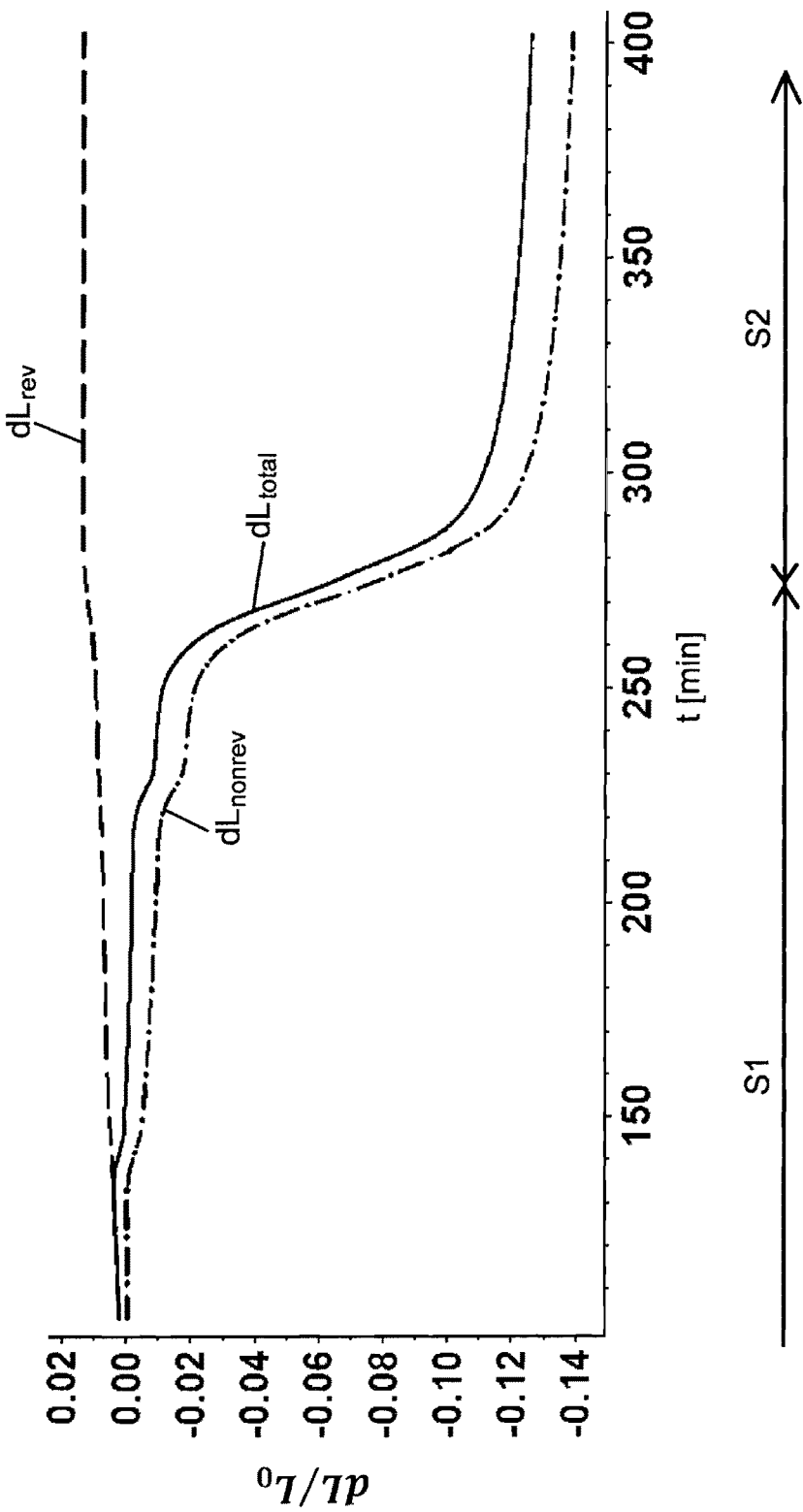
FIG. 7 shows a diagram to illustrate the result of a thermomechanical analysis according to the third example and FIG. 8 shows a device for the thermomechanical analysis of a sample according to an exemplary embodiment.

FIGS. 6 and 7 show another example of a dilatometric analysis according to the invention of a sample made of a ceramic.

FIG. 6 shows the modulated temperature program used which has a first modulated segment S1 in the time interval from about 100 to 280 min and immediately following this, a second modulated segment S2 in the time interval from about 280 to 400 min.

In the first modulated segment S1 the temperature program has a first basic heating rate β1 of about 5 K/min, so that the averaged temperature $T_{avg}$ starting from about 315° C. increases linearly to 1225° C.

In the second segment S2 a substantially lower second basic heating rate β2 of about 0.1 K/min is provided so that the averaged temperature $T_{avg}$ starting from about 1225° C. (end temperature of the first segment S1) now increases linearly by about 10° C. to about 1235° C.

The sample studied here shows several thermally induced conversion processes in the course of the temperature program, namely at temperatures of about 500° C., 945° C. and 1130° C. Whereas the first two "effects" (at 500° C. and 945° C.) therefore lie in the first segment S1, the last effect (at 1130° C.) extends over the boundary between the two segments. The effect is already beginning at about 1130° C. and is not yet ended at 1225° C.

For the calculation of the corrected reversible component $dL_{rev\text{-}corr}$ (see FIG. 7) of the directly measured total length variation $dL_{total}$ (FIG. 6), a correction parameter k was calculated in a temperature-dependent manner using data from the first segment S1 and specifically in a range of S1 in which no thermal effect occurs, i.e. for example, using data from the time interval from about 100 to 130 min, corresponding to a temperature range of about 315 to 470° C.

The correction parameter k was here again calculated in the form of an estimate of the temperature-dependent function of the ratio of the total coefficient of thermal expansion $\alpha_{total}$ and the reversible coefficient of thermal expansion $\alpha_{rev}$, where these expansion coefficients were obtained from data measured directly in the range [100 min, 130 min] or [315° C., 470° C.] or known previously ($T_{avg}$, $\Delta T$, L, dL). In the simplest case, for example, a linear function can be used as the estimating function (variation of k proportional to the variation of the temperature). Notwithstanding this however, more complex estimating functions. e.g. polynomials of at least the second degree, could be used.

The correction parameter k calculated in this way as a temperature-dependent function is advantageously used however not only for the intended correction in the range [100 min, 130 min] or [315° C., 470° C.] but (by extrapolation) over the entire modulated temperature program, i.e. [100 min, 400 min] or [315° C., 1235° C.].

Unlike the example described (FIGS. 6 and 7) in which in segment S2 a low but non-vanishing basic heating rate $\beta2$ of about 0.1 K/min is provided, the basic heating rate $\beta2$ used in the second segment S2 could also be zero. A very low second basic heating rate or $\beta2=0$, for example, can then be advantageous if at the beginning of the second segment, the temperature is so high that a further increase in temperature in the course of the second segment S2 presents difficulties with the apparatus.

Also unlike the example described (FIGS. 6 and 7) in which the second segment S2 when considered in time, follows the first segment S1, within the framework of the invention the second segment S2 (with lower heating rate $\beta2$) could also precede the first segment S1 (with high heating rate $\beta1$). This would be meaningful, for example, if the sample to be studied undergoes one or several thermally induced conversion processes at rather low temperatures whereas no such conversion processes take place at rather high temperatures. Also then the correction parameter k calculated in a suitable segment S1 (containing a region without thermally induced conversion processes) of the temperature program for this purpose can be extrapolated to a certain extent into the temporally preceding (at lower temperatures) second segment S2 and used there to calculate the profiles of $dL_{rev\text{-}corr}$ and/or $\alpha_{rev\text{-}corr}$.

According to the method of analysis described above it is advantageously possible at the same time to perform an analysis for dynamic segments (heating rate $\beta1$ greater than or less than 0) and almost isothermal segments ($\beta2=0$), or almost isothermal segments ($\beta2<\beta1$ or $\beta2\ll\beta1$).

The temperature-modulated measurements provided according to the invention can advantageously be extended into a relatively high temperature range, e.g. up to final temperatures of $T_{avg}$ higher than 1000° C., in particular higher than 2000° C., approached operationally by the temperature program so that a possible application is, for example, the analysis or characterization of the sintering behaviour of ceramics.

A calibration of the measurement of reversible material parameters (such as $dL_{rev}$ and $\alpha_{rev}$) performed for a dynamic segment ($\beta\neq0$) of the temperature program by means of a correction parameter k can advantageously be taken into account in the calculation of the analysis result for one or more other segments, in particular for example for a directly preceding or a directly following segment (in particular, for example, with a relatively low selected $\beta$ or even 0).

Figure 8:
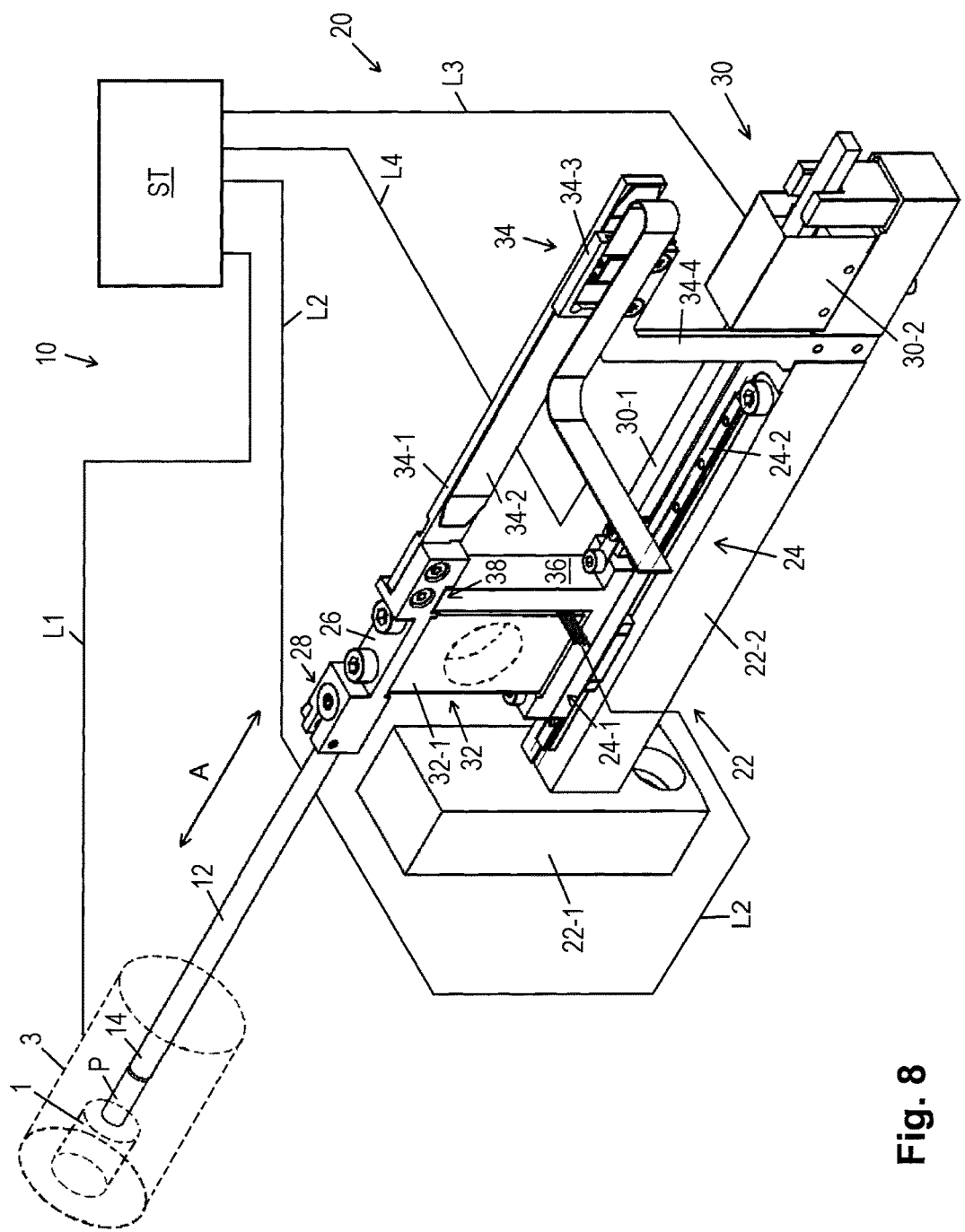

FIG. 8 shows an exemplary embodiment of an apparatus 10 for carrying out a method of analysis of the type described here. In this example the apparatus 10 is used as part of a thermomechanical analysis (TMA) (alternatively the apparatus 10 could also be operated in a DMA (dynamic mechanical analysis) mode, i.e. with variable force loading).

Some of the components of the apparatus are shown as dashed lines in FIG. 8, namely a sample holder 1 in a controlled temperature-controlled furnace 3 for mounting and controllable temperature control of a sample P on which the TMA measurement is to be carried out.

In the measurement the length variation (here resulting, for example, from a temperature-modulated heating or cooling of the sample P in the furnace 3) is measured in a direction which is subsequently designated as longitudinal direction and is indicated by the double arrow A in FIG. 8. In addition, in the measurement the sample P is exposed to a predetermined constant small force loading (e.g. about 0.1 N) which also acts on the sample P in the longitudinal direction A.

During the measurement of the length (variation), the sample P received by the sample holder 1 is temperature-controlled according to a modulated temperature program (e.g. of the type already described) and the force applied to the sample is regulated to a predetermined constant value.

The apparatus 10 comprises a sensing stamp 12 which during the measurement exerts the predetermined force (here: compressive force) onto the sample P with a sensing stamp end 14.

In this application, the material of the sensing stamp should have the lowest possible or at least well defined thermal expansion so that this thermal expansion has little influence on the measurement result or can be taken account accordingly as part of a control program and/or a subsequent evaluation. The same applies to the material of the sensing stamp holder.

The apparatus 10 further comprises a measuring device 20 to which the sensing stamp 12 is attached and by means of which the movement of the sensing stamp 12 resulting from the length variation of the sample P in the longitudinal direction A is measured during the measurement. The measuring device 20 comprises:

a stationary base 22 which in the example shown comprises a first base part 22-1 (e.g. for holding the furnace 3 in relation to the measuring device 20) and a second elongate base part 22-2 extending in longitudinal direction A, a sensing stamp holder 26 mounted movably on the stationary base 22 by means of a guide device 24 in longitudinal direction A relative to the stationary base 22, on which the sensing stamp 12 is fastened by means of a screw clamp 28 in the example shown, a controllable drive device 30 for driving the sensing stamp holder 26 in longitudinal direction A relative to the stationary base 22, a force measuring device 32 for detecting the force exerted by the sensing stamp 12 on the sample P, a control device ST which is configured to control the drive device 30 depending on the force detected by means of the force measuring device 32 according to the predetermined force loading and a displacement transducer 34 for measuring the movement of the sensing stamp 12 in longitudinal direction A relative to the base 22.

The function of the apparatus 10 shown can be described as follows:

Starting from the situation shown in FIG. 8 which the sample P is already disposed on the sample holder 1 in the furnace 3 and is contacted at the end facing away from the sample holder 1 by the sensing stamp end 14, a "TMA measurement program" is performed by means of a control program running in the control device ST, which consists in heating the sample P according to the temperature program, preloading the sample P here by means of the sensing stamp 12 according to the force specification (here: time-independent compressive force) and measuring the resulting length variation of the sample P in longitudinal direction A in the time behaviour.

For this purpose the control device ST is connected via control lines L1, L2, L3 and L4 to corresponding apparatus components: the line L1 is used to transmit a temperature-control signal to the furnace 3 or a temperature-control device integrated therein (e.g. electrical heater). In addition, a temperature signal measured for example by means of a thermocouple on the sample P can be transmitted back to the control device ST via the line L1. The line L2 is used to transmit a force measurement signal (measured value of the force exerted on the sample P) from the force measuring device 32 to the control device ST. The line L3 is used to transmit a drive control signal to the drive device 30. The line L4 is used to transmit a distance measurement signal output from the displacement transducer 34.

In particular, the time-dependent temperature signal (representative of the temperature T) transmitted, for example, via the line L1 and the time-dependent length variation signal (representative for example of the absolute length variation dL) transmitted via the line L4 is stored in the control device ST to be available for a corresponding evaluation after the end of the measurement.

During the measurement the control device ST controls the force applied by means of the sensing stamp 12 to the sample P by means of a control of the drive device 30. This functions as follows: the sensing stamp 12 is attached to the sensing stamp base 26 as already mentioned by means of the screw clamp 28 so that a corresponding loading or adjustment of the sensing stamp holder 26 is transmitted directly to the sensing stamp 12 and thus further to the sample P.

In the example shown the sensing stamp holder 26 is not driven directly by the drive device 30. On the contrary as can be seen in FIG. 8, the sensing stamp holder 26 is connected (here: screwed) to an upper end of an elastic body 32-1 in the figure, the lower end of which in FIG. 8 is connected (here: screwed) to a carriage 24-1 of the guide device 24 which is guided movably in longitudinal direction A on a guide rail 24-2 of the guide device 24 and is accordingly movably by means of a push rod 30-1 of the drive device 30. As can be seen in the figure, the end of the push rod 30-1 is screwed onto the carriage 24-2. Accordingly a driving of the drive device 30 which, in the example shown contains a piezo step motor driven via the line L3, initially brings about a displacement of the push rod 30-1 and therefore of the carriage 24-1 in longitudinal direction A. Via the elastic body 32-1, this carriage movement is converted via the sensing stamp holder 26 and the sensing stamp 12 into a corresponding force or force variation on the sample P.

Accordingly, the unit formed from the carriage 24-1, the sensing stamp holder 26 and the interposed elastic body 32-1 can also be designated as drivable "sensing stamp base" which is mounted movably on the stationary base 22 via the guide device 24 in longitudinal direction A relative to the stationary base 22 and on which the sensing stamp 12 is fastened (or can be fastened). The sensing stamp base 24-1, 26, 32-1 is driven in longitudinal direction A relative to the stationary base 22 by the controllable drive device 30 s explained.

The elastic body 32-1 together with a (not shown in the figures) strain measuring strip (e.g. attached to an outer surface of the elastic body 32-1) connected to the line L2 forms the force measuring device 32.

In particular when the elastic body 32-1 is formed from a metallic material, instead of a solid material a material recessed, for example at least in a central region can be used, as symbolized by the dashed line in FIG. 8 (here: circular recess in a rectangular body). Notwithstanding this, a plurality of respectively smaller such recesses of the elastic body could be provided.

By means of the force measuring device 32, during the measurement the force actually applied to the sample P is measured as a function of time and preferably supplied as an analogue/digital converted signal via the line L2 to the control device ST (or analogue/digital converter in the control device).

The force loading predefined by a corresponding user input, i.e. the force ("desired value") to be applied to the sample P is also stored in the control device ST. By means of the control program running in the control device ST, the measured "actual value" of the force is regulated by appropriate control of the driving device 30 to the "desired value" predefined by the predefined force loading. Advantageously an unavoidable friction in practice in the region of the guide device 24 (between carriage 24-1 and guide rail 24-2) does not result in a corresponding falsification of the force measurement.

Likewise, the measurement of the length variation of the sample P performed simultaneously in the exemplary embodiment shown does not result in a falsification of the force measurement. In the example shown the measurement of the length variation is accomplished as follows: a straightedge carrier 34-1 with straightedge 34-2 formed therefrom or attached thereon (e.g. glued) in the example shown is mounted on the sensing stamp holder 26 whose movement in longitudinal direction A corresponds to the length variation of the sample P to be measured so that the length variation of the sample P is converted into a corresponding shift of the straightedge 34-3 which can thus be measured simply.

For this purpose the displacement transducer 34 further comprises a stationarily held optical sensor 34-3 for measurement of the relative displacement between this sensor 34-3 and the straightedge 34-2. For this purpose the straightedge 34-3 is for example provided or configured with stroke markings distributed equidistantly over its length, which are detected when the optical sensor 34-3 and a linear coding electronics connected thereto (or integrated therein) runs past the straightedge 34-3 in order to obtain a representative measurement signal for the length variation of the sample P (the number of detected markings is a measure for the length variation). This measurement signal is supplied via the line L4 to the control device ST and there stored digitally for a subsequent evaluation as a time-dependent sample length signal.

The linear coding electronics can, for example, be disposed in the region of the optical sensor 34-3 or alternatively in the region of the control device ST.

In the example shown the stationary holding of the optical sensor 34-3 is accomplished by a holder 34-4 which on the one hand is connected to the sensor 34-3 (here: screwed) and on the other hand is connected to the base 22 (here: screwed).

By means of the apparatus 10 shown, the length variation of the sample P loaded with a predetermined force in longitudinal direction A can thus be measured advantageously as part of a TMA analysis where the movement of the sensing stamp 12 resulting from the length variation of the sample P in longitudinal direction A is measured without contact, where sensing stamp base 24-2, 26, 32-1 on which the sensing stamp 12 is fastened, is driven in longitudinal direction A relative to the stationary base 22 and where this driving is accomplished by means of the control software depending on the force applied by the sensing stamp 12 to the sample P and detected by means of the force measuring device 32 according to the predetermined force loading (force regulation).

The recorded data are subjected to an evaluation by means of the software running in the control device ST in order to determine temperature-dependent profiles of the reversible and non-reversible components of the length variation dL (or dL/L) or the coefficient of thermal expansion α. By appropriate configuration of this software, in particular the embodiments and further developments described further above for the method of analysis can be implemented.

What is claimed is:

1. A method for the thermomechanical analysis of a sample (P) of a material comprising
   a) arranging the sample (P) in a thermomechanical analysis device and controlling the temperature of the sample (P) by means of the analysis device according to a modulated temperature program,
   b) recording data obtained by means of the analysis device which is representative of a length variation (dL) of the sample (P) in the course of the modulated temperature program,
   c) evaluating the data in order to determine a reversible component ($dL_{rev}$) of the length variation (dL) or a reversible component ($\alpha_{rev}$) of the coefficient of thermal expansion ($\alpha$) of the sample (P),
   d) calculating a corrected reversible component ($dL_{rev\text{-}corr}$; $\alpha_{rev\text{-}corr}$) of the length variation (dL) or of the coefficient of thermal expansion ($\alpha$) by means of a correction parameter (k), the correction parameter (k) being calculated as a ratio which is determined from data of a parameter ($\alpha_{total}$) characterizing a total length variation ($dL_{total}$) and data of a parameter ($\alpha_{rev}$) characterizing the reversible component ($dL_{rev}$) of the length variation (dL),
   characterized in that the temperature program has a first segment (S1) with a first basic heating rate ($\beta1$) and the correction parameter (k) is calculated using data from the first segment (S1) in a temperature-dependent manner from an estimate of a temperature-dependent function of said ratio in a region of the first segment (S1) in which the sample (P) is not subjected to any thermally induced conversion process, and that the temperature program has a second segment (S2) with a second basic heating rate ($\beta2$) and the correction parameter (k) calculated using the data from the first segment (S1) is used to calculate the corrected reversible component ($dL_{rev\text{-}corr}$; $\alpha_{rev\text{-}corr}$) of the length variation (dL) or the coefficient of thermal expansion ($\alpha$) in the second segment (S2).

2. The method according to claim 1, wherein the magnitude of the second basic heating rate ($\beta2$) is equal to the magnitude of the first basic heating rate ($\beta1$).

3. The method according to claim 1, wherein the magnitude of the second basic heating rate ($\beta2$) is smaller than the magnitude of the first basic heating rate ($\beta1$).

4. The method according to claim 1, wherein the magnitude of the first basic heating rate ($\beta1$) is greater than 0.5 K/min, in particular greater than 1 K/min.

5. The method according to claim 1, wherein the magnitude of the second basic heating rate ($\beta2$) is less than 0.5 K/min, in particular less than 0.2 K/min.

6. The method according to claim 1, wherein the magnitudes of the first basic heating rate ($\beta1$) and the second basic heating rate ($\beta2$) differ from one another by at least a factor of 2, in particular at least a factor of 5.

7. The method according to claim 1, wherein the sample (P) undergoes a thermally induced process within the second segment (S2).

8. The method according to claim 1, wherein the temperature (T) of the sample (P) increases in the course of the second segment (S2) and exceeds a value of 500° C., in particular exceeds a value of 1000° C.

9. The method according to claim 1, wherein during evaluation of the data a non-reversible component ($dL_{nonrev}$) of the length variation (dL) is further determined.

10. The method according to claim 1, wherein for the correction parameter (k) calculated using data from the first segment (S1), a mathematical estimating function is modelled which gives the correction parameter (k) as a function of the temperature (T) of the sample (P) and wherein by using the mathematical estimating function, the correction parameter (k) to be used to calculate the corrected reversible component ($dL_{rev\text{-}corr}$) of the length variation (dL) in the second segment (S2) is calculated.

11. The method according to claim 1, wherein in the course of the temperature program the second segment (S2), when considered in time, lies directly after the first segment (S1) or conversely.

12. An apparatus for the thermomechanical analysis of a sample (P) of a material comprising
   a sample holder for receiving the sample (P),
   a temperature-control device for controlling the temperature of the sample (P) according to a modulated temperature program,
   a temperature-measuring device for measuring a temperature (T) of the sample (P) in the course of the modulated temperature program,
   a length measuring device for measuring a length variation (dL) of the sample (P) in the course of the modulated temperature program,
   a data recording device for recording data which are representative for the length variation (dL) of the sample (P) in the course of the modulated temperature program and data which are representative for the variation in the temperature (dT) of the sample (P) in the course of the modulated temperature program,
   an evaluation device which is configured to determine a reversible component ($dL_{rev}$) of the length variation (dL) or a reversible component ($\alpha_{rev}$) of the coefficient of thermal expansion ($\alpha$) of the sample (P), the evaluation device being configured to calculate a corrected reversible component ($dL_{rev\text{-}corr}$; $\alpha_{rev\text{-}corr}$) of the length variation (dL) or of the coefficient of thermal expansion ($\alpha$) by means of a correction parameter (k), the correction parameter (k) being calculated as a ratio which is determined from data of a parameter ($\alpha_{total}$) characterizing a total length variation ($dL_{total}$) and data of a parameter ($\alpha_{rev}$) characterizing the reversible component ($dL_{rev}$) of the length variation (dL), characterized in that the temperature control device is configured, in the course of the modulated temperature program, to provide a first segment (S1) with a first basic heating rate ($\beta$1) and a second segment (S2) with a second basic heating rate ($\beta$2), and that the evaluation device is configured to calculate the correction parameter (k) using data from the first segment (S1) in a temperature-dependent manner from an estimate of a temperature-dependent function of the said ratio in a region of the first segment (S1) in which the sample (P) is not subjected to any thermally induced conversion process and to use the correction parameter (k) calculated using the data from the first segment (S1) for calculating the corrected reversible component ($dL_{rev\text{-}corr}$; $\alpha_{rev\text{-}corr}$) of the length variation (dL) or the coefficient of thermal expansion ($\alpha$) in the second segment (S2).

\* \* \* \* \*